US011009514B2

(12) United States Patent
Bazan et al.

(10) Patent No.: US 11,009,514 B2
(45) Date of Patent: May 18, 2021

(54) METHODS OF DETECTING, DIAGNOSING, AND TREATING CAROTID PLAQUE VULNERABILITY

(71) Applicant: Ochsner Health System, New Orleans, LA (US)

(72) Inventors: Hernan A. Bazan, New Orleans, LA (US); Yan Lu, New Orleans, LA (US); Song Hong, New Orleans, LA (US); Zhide Fang, New Orleans, LA (US); Bokkyoo Jun, New Orleans, LA (US); Thomas C. Woods, New Orleans, LA (US)

(73) Assignees: OCHSNER HEALTH SYSTEM, New Orleans, LA (US); THE BOARD OF SUPERVISORS OF LOUISIANA STATE UNIVERSITY AND AGRICULTURE AND MECHANICAL COLLEGE, Baton Rouge, LA (US); THE ADMINISTRATORS OF THE TULANE EDUCATIONAL FUND, New Orleans, LA (US)

( * ) Notice: Subject to any disclaimer, the term of this patent is extended or adjusted under 35 U.S.C. 154(b) by 250 days.

(21) Appl. No.: 16/015,453

(22) Filed: Jun. 22, 2018

(65) Prior Publication Data
US 2018/0372763 A1   Dec. 27, 2018

Related U.S. Application Data

(60) Provisional application No. 62/524,262, filed on Jun. 23, 2017.

(51) Int. Cl.
  *G01N 33/92* (2006.01)
  *C07K 16/44* (2006.01)

(52) U.S. Cl.
  CPC ............. *G01N 33/92* (2013.01); *C07K 16/44* (2013.01); *G01N 2405/00* (2013.01); *G01N 2800/323* (2013.01); *G01N 2800/324* (2013.01); *G01N 2800/52* (2013.01)

(58) Field of Classification Search
  CPC ............. G01N 33/92; G01N 2800/324; G01N 2800/52; G01N 2800/323; G01N 2405/00
  See application file for complete search history.

(56) References Cited

FOREIGN PATENT DOCUMENTS

WO   2008/058274 A2   5/2008

OTHER PUBLICATIONS

Guilbault, Claudine et al. "Cystic fibrosis fatty acid imbalance is linked to ceramide deficiency and corrected by fenretinide." Am J Respir Cell Mol Biol (2009) 41 100-106. (Year: 2009).*
Wiese, Rick et al. "Simultaneous multianalyte ELISA performed on a microarray platform." Clinical Chemistry (2001) 47 (Year: 2001) 1451-1457.*
Bazan, et al., Acute Loss of miR-221 and miR-222 in the Atherosclerotic Plaque Shoulder Accompanies Plaque Rupture (2015); From the Section of Vacsular and Endoscular Surgery, Department of Surgery (H.A.B., A.J.B.) and Laboratory of Molecular Cardiology (C.B.O.) Ochsner Clinic, New Orleans, LA; and Tulane Heart and Vascular Institute and the Department of Physiology, Tulane School of Medicine, New Orleans, LA; doi: 10.1161/STROKEAHA. 115.010567.
Bazan, et al., "Carotid Plaque Rupture is Accompanied by an Increase in the Ratio of Serum circR-284 to miR-221 Levels" (2017); From the Section of Vascular and Endovascular Surgery, Department of Surgery, Ochsner Clinic, New Orleans, LA (H.A.B., A.J.B.); the University of Queensland School of Medicine, Ochsner Clinical school, New Orleans, LA (H.A.B., A.J.B.); and Department of Physiology and the Heart & Vascular Institute, Tulane School of Medicine, New Orleans, LA (S.A.H., A.B., A.J.B., D.L., T.C.W.); doi: 10.1161/circgenetics.117.001720.
Bazan, et al., "Circulating inflammation-resolving lipid mediators RvD1 and DHA are decreased in patients with acutely symptomatic carotid disease", Prostaglandins, Leukotrienes and Essential Fatty Acids 125(2017); p. 43-47.
Paloschi, et al., "Towards Point-of-Care Measurements Using Noncoding RNAs: A Novel Tool to Monitor Aggravation of Advanced Atherosclerotic Lesions" (2017); From the Department of Vascular and Endovascular Surgery, Klinikum rechts der Isar, Technical University Munich, Germany (V.P., L.M.); and Department of Medicine, Center for Molecular Medicine, Karolinska Institute, Stockholm, Sweden (L.M.); doi: 10.1161/CIRCGENETICS.117. 001859.
Bazan, et al., "Diminished omega-3 fatty acids are associated with carotid plaques from neurologically symptomatic patients: Implications for carotid interventions" Vascular Pharmacology 51 (2009) 331-336.
Schwanke, et al., "EPA- and DHA-derived resolvins' actions in inflammatory bowel disease" European Journal of Pharmacology 785 (2016) 156-164.

(Continued)

*Primary Examiner* — Christopher Adam Hixson
(74) *Attorney, Agent, or Firm* — Schwabe Williamson & Wyatt, PC

(57) ABSTRACT

Disclosed are methods of, and assay and kits for, detecting and diagnosing methods of detecting, diagnosing, vulnerable carotid artery disease capable of becoming acutely symptomatic using the levels of Resolvin D1 (RvD1), docosahexaenoic acid (DHA), and arachidonic acid (AA). Also disclosed are methods of treating carotid artery disease and methods of identifying agents for use in the treatment of carotid artery disease.

18 Claims, 5 Drawing Sheets

(56) References Cited

OTHER PUBLICATIONS

Fredman, et al., "An imbalance between specialized pro-resolving lipid mediators and pro-inflammatory leukotrienes promotes instability of atherosclerotic plaques" Nature Communications 7:12859; (2016) 11 pages.

Merched, et al., "Atherosclerosis: evidence for impairment of resolution of vascular inflammation governed by specific lipid mediators" The FASEB Journal, vol. 22 Oct. 2008; 3595-3606.

Upadhyah, "Emerging Risk Biomarkers in Cardiovascular Diseases and Disorders" Journal of Lipids, vol. 2015, article ID 971453; 50 pages.

Eickmeier, et al., "Pro-resolving lipid mediator Resolvin D1 serves as a marker of lung disease in Cystic Fibrosis" PLoS One 12(2):e0171249; published Feb. 3, 2017; 12 pages.

\* cited by examiner

FIG. 3C

| Lipid mediators | AUC | 95% Confidence Interval | P value | Sensitivity | Specificity | LR+ | LR- | Accuracy |
|---|---|---|---|---|---|---|---|---|
| DHA | 0.6905 | (0.5312, 0.8497) | 0.0191 | 0.7143 | 0.6667 | 2.1429 | 0.4285 | 0.6889 |
| AA | 0.756 | (0.6122, 0.8997) | 0.0005 | 0.6667 | 0.8333 | 4 | 0.4 | 0.7556 |
| RvD1 | 0.7619 | (0.6178, 0.9061) | 0.0004 | 0.8571 | 0.6667 | 2.5714 | 0.2142 | 0.7556 |
| AA : DHA | 0.8611 | (0.7525, 0.9698) | <0.0001 | 0.9048 | 0.7083 | 3.102 | 0.1345 | 0.8 |
| DHA : RvD1 | 0.5595 | (0.3804, 0.7387) | 0.515 | 0.6191 | 0.625 | 1.6508 | 0.6095 | 0.6222 |
| AA : RvD1 | 0.8353 | (0.7097, 0.9609) | <0.0001 | 0.7143 | 0.9167 | 8.5714 | 0.3117 | 0.8222 |
| Sum of normalized DHA/AA and RvD1/AA | 0.90 | (0.8069, 0.9807) | <0.0001 | 0.8571 | 0.8333 | 5.1429 | 0.1714 | 0.8444 |

1

METHODS OF DETECTING, DIAGNOSING, AND TREATING CAROTID PLAQUE VULNERABILITY

CROSS-REFERENCE TO RELATED APPLICATION

This application claims to the priority benefit of the earlier filing date of U.S. Provisional Application No. 62/524,262, filed Jun. 23, 2017, which is hereby incorporated herein in its entirety.

STATEMENT OF GOVERNMENT SUPPORT

This invention was made with government support under grant numbers P30 GM103340 and R01 DK087800 awarded by the National Institutes of Health. The government has certain rights in the invention.

TECHNICAL FIELD

This disclosure relates to detecting and diagnosing vulnerable carotid artery disease at risk of becoming acutely symptomatic and causing stroke and treating carotid artery disease. Specifically, newly discovered biomarkers, and novel methods for using them, are described, including predicting which patients harbor a vulnerable carotid plaque; that is, patients with asymptomatic carotid disease at risk of conversion to the acutely symptomatic state.

BACKGROUND

Carotid artery disease occurs when the carotid arteries, located in a person's neck, become narrowed. The carotid arteries are more likely to develop carotid artery disease as a person ages and has risk factors for atherosclerosis, including but not exclusive of hypercholesterolemia, hypertension, diabetes mellitus and tobacco use. Only 1 percent of adults age 50 to 59 have significantly narrowed carotid arteries, but 10 percent of adults age 80 to 89 have this problem.

Arteries are normally smooth and unobstructed on the inside, but as one ages, fat can accumulate in the walls of the artery causing inflammation. This combination leads to the development of atherosclerotic plaques. Atherosclerotic plaques arise in the vessel intima and media and are thought to be a result of cholesterol deposition, hemodynamic strain, and inflammation (P. Libby et al., Inflammation and atherosclerosis, Circulation, 105 (2002) 1135-1143).

Rupture of the fibrous cap can lead to a transition from a stable to an unstable atherosclerotic plaque. This plaque rupture can result in clinically relevant sequelae: in the coronary bed, an atherosclerotic plaque rupture leads to myocardial infarction and, in the carotid artery, to an ocular or cerebral ischemic event. These latter events manifest as amaurosis fugax, transient ischemic attacks, or stroke.

Gaps in knowledge remain in the mechanisms leading to acute symptomatic atherosclerotic plaque rupture. Increasing evidence suggests that unresolved inflammation contributes to the development of plaque rupture (see G. Fredman et al., Nature communications, 7 (2016) 12859; A. J. Merched et al., FASEB journal: official publication of the Federation of American Societies for Experimental Biology, 22 (2008) 3595-3606; and H. A. Bazan et al., Vascul Pharmacol, 51 (2009) 331-336).

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIGS. 3A-3C are graphs and a table of potential composite biomarkers: concentration ratios of the resolving lipid mediator RvD1 to omega-3 docosahexaenoic acid (DHA) or to omega-6 arachidonic acid (AA) and their receiver operating characteristic (ROC) analysis. FIG. 3A is a bar graph showing concentration ratios of AA:DHA, AA:RvD1, and DHA:RvD1 (pM/pM). FIG. 3B or ROC curves of candidate biomarker AA:RvD1 and AA:DHA concentration ratio (pM/pM), as well as the sum of the normalized DHA/AA and RvD1/AA. FIG. 3 C is a table of area under the curve (AUC) of ROC analysis and 95% confidence interval for each candidate biomarker: RvD1, DHA, AA, AA:DHA (pM:pM), DHA:RvD1 (pM/pM), AA:RvD1 (pM/pM), and the sum of the normalized DHA/AA and RvD1/AA.

DETAILED DESCRIPTION OF DISCLOSED EMBODIMENTS

Terms

Figure 1:
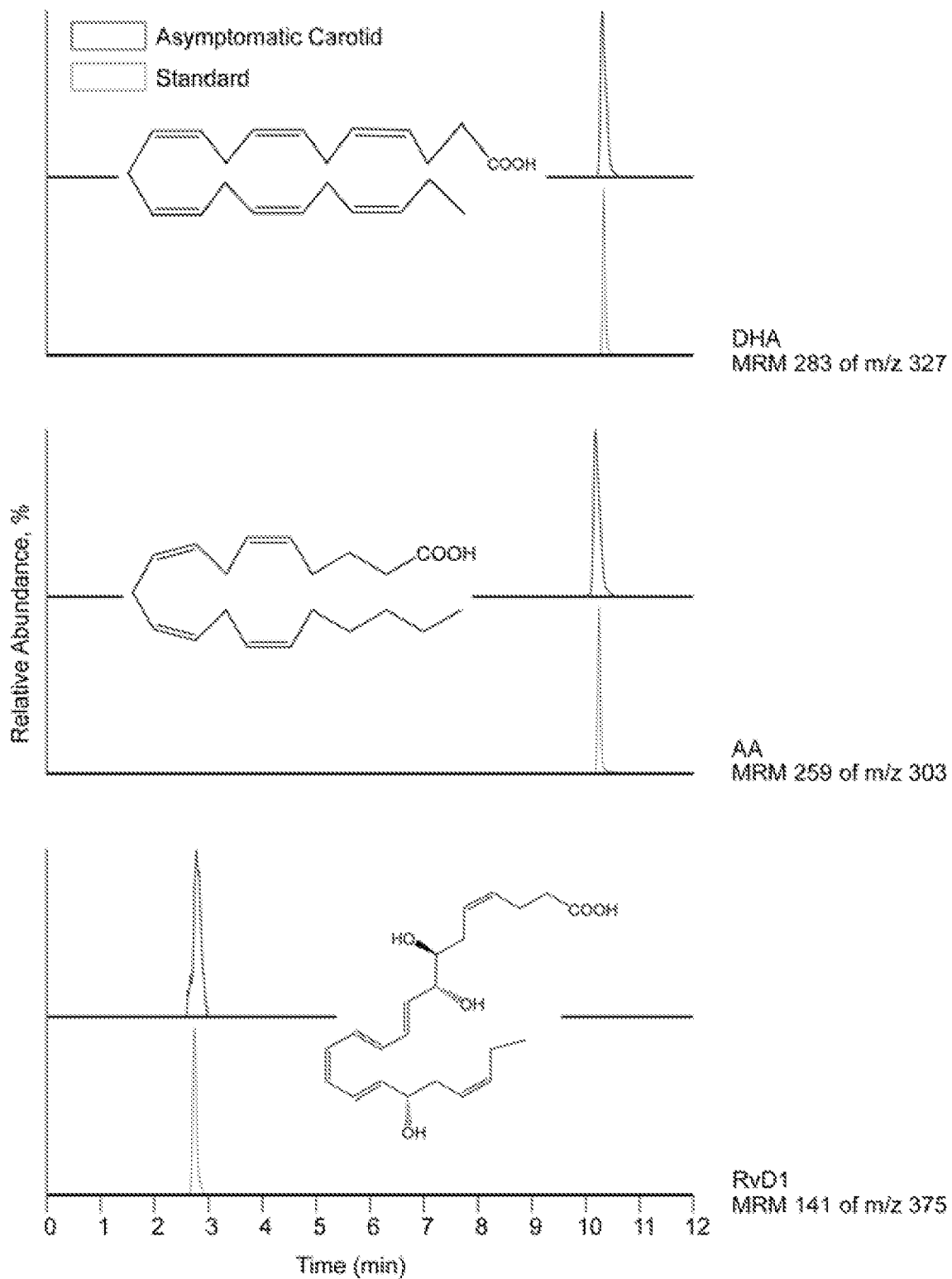
FIG. 1 is a set of typical chromatograms of the select inflammation-resolving lipid mediator RvD1, omega-3 polyunsaturated fatty acid (DHA), and omega-6 polyunsaturated fatty acid arachidonic acid (AA) acquired from a patient's sera using multiple reaction monitoring (MRM) LC-MS/MS.

In the following detailed description, reference is made to the accompanying drawings that form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual,* Cold Spring Harbor Laboratory Press, 1990; and Harlow and Lane, *Using Antibodies: A Laboratory Manual,* Cold Spring Harbor Laboratory Press, 1999. In addition, the materials, methods, and examples are illustrative only and not intended to be limiting.

To facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, and inhalation routes.

Agent: Any protein, lipid, nucleic acid, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including inhibiting or treating arthrosclerosis or a related condition).

Arachidonic acid (AA): A polyunsaturated omega-6 fatty acid 20:4($\omega$-6). Arachidonic acid plays a central role in inflammation related to injury and many diseased states. Arachidonic acid (AA) is the major $\omega$6 PUFA in humans and animals. AA is converted to a large array of short-lived pro-inflammatory eicosanoids including thromboxane A4, leukotriene B4, and sulfido-peptide leukotrienes and generally thought to promote inflammation.

Biological sample: A biological specimen obtained from a subject. Examples include, but are not limited to, saliva, peripheral blood, urine, tissue biopsy, surgical specimen, and autopsy material. In embodiments, the biological sample is blood, or a component thereof, such as plasma or serum.

Contacting: Placement in direct physical association, including both a solid and liquid form. Contacting an agent with a cell can occur in vitro by adding the agent to isolated cells or in vivo by administering the agent to a subject.

Control: A "control" refers to a sample or standard used for comparison with a test sample, such as a sample obtained from a subject or patient (or plurality of patients). In some embodiments, the control is a sample obtained from a healthy patient (or plurality of patients) (also referred to herein as a "normal" control). In some embodiments, the control is a historical control or standard value (e.g. a previously tested control sample or group of samples that represent baseline or normal values, such as baseline or normal values in a normal subject or subject in who does not have carotid artery disease). In some examples the control is a standard value representing the average value (or average range of values) obtained from a plurality of patient samples (such as an average value or range of values of DHA, RvD1 and/or AA from normal patients).

Decrease or downregulate: To reduce the quality, amount, or strength of something. In some examples, when used in reference to a biomarker a (such as a DHA, RvD1 and/or AA), a reduction or downregulation refers to any process which results in a decrease in the level of the biomarker. In certain examples, a decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, biopsy, and the methods disclosed herein.

Diagnostically significant amount: As used herein a "diagnostically significant amount" refers to an increase or decrease in the level of a biomarker, such as DHA, RvD1 and/or AA, or ratio thereof, such the ratio of AA:RvD1 and/or AA:DHA in a biological sample that is sufficient to allow one to distinguish one patient population from another (such as a subject suffering an atherosclerosis from one that is not). In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control. In some embodiments, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold change in the ratio of two or more biomarkers relative to a control.

Controls or standards for comparison to a sample include samples believed to be normal as well as laboratory values (e.g., range of values), even though possibly arbitrarily set, keeping in mind that such values can vary from laboratory to laboratory. Laboratory standards and values can be set based on a known or determined population value and can be supplied in the format of a graph or table that permits comparison of measured, experimentally determined values.

Docosahexaenoic acid (DHA): An omega-3 fatty acid that is a primary structural component of the human brain, cerebral cortex, skin, and retina. DNA's structure is a carboxylic acid with a 22-carbon chain and six cis double bonds; with the first double bond located at the third carbon from the omega end.

Effective amount: An amount of agent that is sufficient to generate a desired response, such as reducing or inhibiting one or more signs or symptoms associated with a condition or disease. When administered to a subject, a dosage will generally be used that will achieve target tissue concentrations. In some examples, an "effective amount" is one that treats one or more symptoms and/or underlying causes of any of a disorder or disease.

Patient or Subject: A term that includes human and non-human animals, such as those having arterial plaques. In one example, the patient or subject is a mammal, such as a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 19th Edition (1995), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Resolvin: Anautacoids of a specific lipid structure: dihydroxy or trihydroxy metabolites of omega-3 fatty acids, primarily eicosapentaenoic acid (EPA) and docosahexaenoic acid (DHA) but also the docosapentaenoic acid (DPA), clupanodonic acid. They are members of an expanding class of polyunsaturated fatty acid (PUFA) metabolites termed specialized proresolving mediators (SPMs). Metabolically stable analogs of the SPMs, including the resolvins, are in development and being tested in volunteers with chronic inflammation-related diseases.

Resolvin Ds (RvDs) are poly-hydroxyl metabolites of DHA. To date, six RvD's, which vary in the number, position, and chirality of their hydroxyl residues as well as the position and cis-trans isomerism of their 6 double bonds, have been described. These are: RvD1 (7S,8R,17S-trihydroxy-DHA), RvD2 (7S,16R,17S-trihydroxy-DHA), RvD3 (4S,7R,17S-trihydroxy-DHA), RvD4 (4S,5,17S-trihydroxy-DHA; chirality at position 5 not yet determined), RvD5 (7S,17S-dihydroxy-DHA), and RvD6 (4S,17S-dihydroxy-DHA). Resolvins, including RvD1, are inflammation-resolving mediators initially uncovered in the resolution phase of inflammation. DHA-derived RvD1 contributes to the atherosclerotic plaque stabilization by DHA (see G. Fredman et al., Nature communications, 7 (2016) 12859).

Treating a disease: A phrase referring to a therapeutic intervention that ameliorates a sign or symptom of a disease or pathological condition after it has begun to develop.

Upregulated or activated: To increase the quality, amount, or strength of something. In some examples, when used in reference to a biomarker a (such as a DHA, RvD1 and/or AA), upregulated or activated refers to any process which results in an increase in the level of the biomarker. In certain examples, the increase is at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Overview of Several Embodiments

Introduction

Efficient biomarkers for early prediction and diagnosis of acute symptomatic plaques are lacking. This impedes the ability of physicians to promptly diagnose and treat patients presenting with an atherosclerotic plaque rupture event. Minimizing the time between plaque rupture and treatment is critical in reducing the morbidity after a patient has sustained a stroke as select patients diagnosed within 3 hours are offered systemic thrombolysis with recombinant tissue plasminogen activator (tPA), which improves outcomes after stroke (J. L. Saver et al., JAMA: the journal of the American Medical Association, 309 (2013) 2480-2488). However, tPA utilization rates among acute ischemic stroke patients is less than 7%, mainly due to delay in diagnosis (H. A. Bazan et al., Journal of vascular surgery, 62 (2015) 1529-1538).

Efficient biomarkers for early prediction and diagnosis of an acutely symptomatic carotid plaque rupture event are currently lacking, impairing the ability to diagnose and treat patients with an acute plaque rupture events in a timely fashion. Fibrous cap rupture of a carotid atherosclerotic plaque leads to a transition from a stable to an unstable atherosclerotic plaque and is the etiology of a stroke. A serum biomarker predictive of plaque vulnerability and future stroke risk would be helpful in the management of asymptomatic high-grade carotid stenosis. The stroke reduction benefit from carotid endarterectomy (CEA) over medical therapy in patients with asymptomatic carotid disease is based on randomized controlled trials from the 1990s (Endarterectomy for asymptomatic carotid artery stenosis. Executive Committee for the Asymptomatic Carotid Atherosclerosis Study, JAMA: the journal of the American Medical Association, 273 (1995) 1421-1428.). Since that time, however, both the safety of surgery (CEA) and medical management of carotid disease have improved (S. Chaturvedi et al., Neurology, 87 (2016) 2271-2278). Many now question which is the best therapy for the patient with asymptomatic high-grade carotid disease (S. Chaturvedi et al., Neurology, 87 (2016) 2271-2278). Identification of circulating inflammation-resolving lipid mediators could be used to predict which individuals with high-grade asymptomatic carotid disease are at risk of plaque rupture and stroke. Thus, earlier identification could then be used to treat such patients with more intense medical therapy or with a prophylactic CEA.

As disclosed herein, circulating lipids associated with plaque rupture events were quantitatively profiled via targeted mediator-lipidomics using ultraperformance liquid chromatography tandem mass spectrometry in patients with acutely symptomatic and asymptomatic carotid disease. Endogenous omega-3 and omega-6 polyunsaturated fatty acids (ω3-PUFAs and ω6-PUFAs) and their metabolites likely play crucial roles in atherosclerotic rupture-associated chronic inflammation. The inventors have previously demonstrated that carotid plaques from neurologically symptomatic patients are inflammatory and have decreased intra-plaque levels of ω3 fatty acids, including DHA (see H. A. Bazan et al., Vascul Pharmacol, 51 (2009) 331-336). Consistent with this observation, resolvin D1 (RvD1, 7S, 8R, 17S-trihydroxy-4Z, 9E, 11E, 13Z, 15E, 19Z-docosahexaenoic acid), a potent inflammation-resolving lipid mediator biosynthesized from DHA, was reported recently to promote plaque stability, including decreased lesion oxidative stress and necrosis, improved efferocytosis, and fibrous caps thickening (see G. Fredman et al., Nature communications, 7 (2016) 12859).

As disclosed herein, in a translational model for plaque rupture and utilizing ultraperformance liquid chromatography tandem mass spectrometry, the sera of patients presenting acutely with a symptomatic carotid-related transient ischemic attack or stroke (n=21) were found to have lower Resolvin D1 (RvD1) and docosahexaenoic acid (DHA) levels as compared to patients with asymptomatic carotid disease (n=24). Resolvin D1 (RvD1, 82 pM±11 vs. 152 pM±17, p=0.001) and docosahexaenoic acid (DHA) (52081 pM±6704 vs. 75771 pM±7638, p=0.025) levels were decreased in the sera of patients presenting with an acutely symptomatic carotid plaque rupture event (n=21) compared to patients with asymptomatic (n=24) high-grade carotid stenosis. Circulating arachidonic acid (AA) levels, however, were higher (429188 pM±46484 vs. 257442 pM±35135, p=0.005) in acutely symptomatic compared to asymptomatic carotid patients. In addition ROC curve analysis showed that the serum ratio AA:RvD1 and AA:DHA represent a circulating pro-inflammatory lipid profile that is associated with acutely symptomatic carotid disease and stroke. As disclosed herein ROC curve analysis demonstrated that the serum ratio AA:RvD1 (AUC 0.84, sensitivity 0.71, specificity 0.92) and AA:DHA (AUC 0.86, sensitivity 0.90, specificity 0.71) are biomarkers for the risk of atherosclerotic plaque rupture. Furthermore, a circulating pro-inflammatory lipid profile, characterized by high AA:RvD1 and AA:DHA, was found to be associated with acutely symptomatic carotid disease and stroke. The results presented herein provide a demonstration of the capability of RvD1 as a biomarker for the diagnosis and prediction of acute symptomatic plaque ruptures.

Methods of Detecting Atherosclerosis and Related Conditions

Provided herein is a method of detecting carotid artery disease and related conditions, such as atherosclerosis and/or carotid artery disease in a subject. In embodiments, the methods includes measuring the level of at least one of Resolvin D1 (RvD1), docosahexaenoic acid (DHA), and arachidonic acid (AA) in a biological sample obtained from the subject, such as a serum sample. A decrease in RvD1 and/or DHA and/or an increase in AA, for example, relative to a control, indicates that the subject has an acute atherosclerotic plaque and/or a related condition, such as atherosclerosis. In certain embodiments, the level of RvD1 is detected. In certain embodiments, the level of DHA is detected. In certain embodiments, the level of AA is detected. While the levels of these biomarkers present in serum were found to be altered in subjects with acute atherosclerotic plaques the inventors further found that the ratio of the AA to RvD1 and/or AA to DHA was particularly predictive in detecting acute atherosclerotic plaques. Thus, in embodiments, the ratio of the level of AA to the level of at least one of RvD1 and DHA is determined or calculated. A ratio of AA to RvD1 or DHA greater than a reference value indicative of a no acute atherosclerotic plaque indicates that the subject has an acute atherosclerotic plaque and/or atherosclerosis or a related disease or disorder. In some embodiments, an increase in the level of AA indicates an acute atherosclerotic plaque and/or atherosclerosis or a related disease or disorder, for example relative to a control. In embodiments, a decrease in the level of RvD1 and/or DHA indicates acute atherosclerotic plaque and/or atherosclerosis or a related disease or disorder, for example relative to a control. In some embodiments, the increase or decrease in the level of the AA, RvD1 and/or DHA is of a diagnostically significant amount. In some embodiments, the method is used for diagnosing or prognosing or prediction of acute symptomatic plaques. In some embodiments, the method is used for diagnosing or prognosing acute atherosclerotic plaque rupture.

In some embodiments of the methods, the diagnostically significant increase or decrease in the level of AA, RvD1 and/or DHA is at least a 1.1-fold, 1.2-fold, 1.3-fold, 1.4-fold, 1.5-fold, 2-fold, 3-fold, 4-fold, 5-fold, 10-fold increase or decrease, for example relative to the level of a control. In some examples, the ratio of AA to RvD1 and/or DHA is at least 1.1, 1.2, 1.3, 1.4, 1.5, 2, 3, 4, 5, 6, 7, 8, 9, 10, 15, 20, 30, 50, 60, 70, 80, 100, or even greater. Thus in some embodiments, a ratio AA to RvD1 and/or DHA of at least 1.1, 1.2, 1.3, 1.4, 1.5, 2, 3, 4, 5, 6, 7, 8, 9, 10, 15, 20, 30, 50, 60, 70, 80, 100, or even greater is used as a control threshold, above which atherosclerosis and related conditions are diagnosed or detected.

Methods of detecting and measuring AA, RvD1 and/or DHA are known in the art and are described in detail below.

In some embodiments of the methods, the biological sample is blood, or a component thereof, such as plasma or serum. Thus, the method in some examples includes obtaining an appropriate sample from the patient to be diagnosed or treated with the methods provided herein.

In some embodiments, the method further includes providing an appropriate therapy for the subject diagnosed with an acute atherosclerotic plaque rupture. In some examples, the therapy includes administering an agent that increases the level of RvD1 relative to a control. In some examples, the therapy includes administering RvD1 or a derivative thereof to the subject. In some embodiments, the therapy includes surgical intervention or a recommendation of such intervention, such as rapid carotid revascularization, carotid endarterectomy, bypass surgery, or other surgical interventions known in the art.

In some embodiments, the method includes selecting a subject with, or believed to have, arthrosclerosis. In some embodiments, the method includes selecting a subject with, or believed to have, suffered a myocardial infarction. In some embodiments, the method includes selecting a subject with, or believed to have, suffered a stroke. In some embodiments, the method is used for diagnosing or prognosing a subject with stroke and/or myocardial infarction. In some embodiments, the method includes selecting a subject with, or believed to have, suffered an arterial plaque rupture, or at risk for such a rupture.

In some embodiments, once a patient's diagnosis is determined, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output. In other examples, the output is a numerical value, such as an amount of AA, RvD1, and/or DHA in the sample or a relative amount of AA, RvD1, and/or DHA in the sample as compared to a control. In some examples the numerical value is the ratio of expression of AA to RvD1 and/or DHA. In additional examples, the output is a graphical representation, for example, a graph of the expression and/or ratio of expression on a standard curve or ROC. In a particular example, the output (such as a graphical output) shows or provides a cut-off value or level that indicates the presence of arterial plaque rupture. In some examples, the output is communicated to the user, for example by providing an output via physical, audible, or electronic means (for example by mail, telephone, facsimile transmission, email, or communication to an electronic medical record). The output can provide quantitative information. In some examples, the output is accompanied by guidelines for interpreting the data, for example, numerical or other limits. The output can, for example, include normal or abnormal ranges or a cutoff, which the recipient of the output may then use to interpret the results, for example, to arrive at a diagnosis, prognosis, or treatment plan. In other examples, the output can provide a recommended therapeutic regimen. In some examples, the test may include determination of other clinical information.

In some embodiments, the disclosed methods of diagnosis include one or more of the following depending on the patient's diagnosis: a) prescribing a treatment regimen for the patient if the patient's determined diagnosis is considered to be positive for arterial plaque rupture; b) not prescribing a treatment regimen for the patient if the patient's determined diagnosis is considered to be negative for arthrosclerosis; c) administering a treatment to the patient if the patient's determined diagnosis is considered to be positive for arthrosclerosis; and d) not administering a treatment regimen to the patient if the patient's determined diagnosis is considered to be negative for arthrosclerosis. In an alternative embodiment, the method can include recommending one or more of a)-d). Thus, disclosed is a method of treating a stroke, transient ischemic attack (TIA), myocardial infarction in a subject, arthrosclerosis or a related disorder or disease.

The method can be used, for example, to predict future cardiovascular risk. Specifically, the method can be used to predict risk for myocardial infarction, intermittent claudication, bowel ischemia, retinal ischemia, transient ischemic attacks (TIAs), ischemic strokes, arthrosclerosis or a related disorder or disease, transplant atherosclerosis, unstable angina, sudden death, and other conditions associated with cardiovascular dysfunction. Factors involved in cardiovascular risk include, but are not limited to, serum cholesterol, hypertension, diabetes, sex and age. The method can also be used to assess the severity of a disease, such as atherosclerosis.

Methods are provided herein for evaluating vascular risk, for example for determining whether a subject, such as an otherwise healthy subject, or a subject suspected or at risk of having vascular disease, has vascular disease or will likely develop vascular disease in the future. In particular examples, the method can determine with a reasonable amount of sensitivity and specificity whether a subject has or will likely develop a vascular disease in the future. In some examples, isolated or purified PBMCs, serum, blood or plasma obtained from the subject are used to predict the subject's risk of vascular disease. In one example, the subject is apparently healthy, such as a subject who does not exhibit symptoms of vascular disease (for example has not previously had an acute adverse vascular event such as a myocardial infarction or a stroke). In some examples, a healthy subject is one that if examined by a medical professional, would be characterized as healthy and free of symptoms of vascular disease. In another example, the subject is suspected of having a vascular disease, or is suspected of being at risk of developing a vascular disease in the future. For example, such a subject may have elevated cholesterol or tri-glyceride levels, elevated C-reactive protein levels, or high blood pressure.

The levels of RvD1, DHA, and/or AA in the sera of a subject can be determined using any suitable method. Methods of detecting and optionally quantifying the same are well known in the art (e.g., ELISA, thin layer chromatography, gas chromatography, liquid chromatography, mass and NMR spectrometry, and any combination thereof (e.g., GC/MS), and the like).

The identification and quantification of RvD1, DHA, and/or AA from biological samples, such as those descried herein can be detected and the amount of RvD1, DHA, and/or AA present in the biological sample can be quantified through novel epitopes recognized by polyclonal and/or monoclonal antibodies used in methods such as ELISA, immunoblot assays, flow cytometric assays, immunohistochemical assays, radioimmuno assays, Western blot assays, an immunofluorescent assays, chemiluminescent assays and other polypeptide detection strategies (Wong et al., Cancer Res., 46: 6029-6033, 1986; Luwor et al., Cancer Res., 61: 5355-5361, 2001; Mishima et al., Cancer Res., 61: 5349-5354, 2001; Ijaz et al., J. Med. Virol., 63: 210-216, 2001). Generally these methods utilize antibodies, such as monoclonal or polyclonal antibodies.

Generally, immunoassays for the identification and quantification of RvD1, DHA, and/or AA typically include incubating a biological sample in the presence of antibody, and detecting the bound antibody by any of a number of techniques well known in the art. The biological sample can be peripheral blood including whole blood or any fraction thereof, including sera. The biological sample can be brought in contact with and immobilized onto a solid phase support or carrier such as or other solid support which is capable of immobilizing cells, cell particles or soluble proteins. The support may then be washed with suitable buffers followed by treatment with the antibody that binds RvD1, DHA, or AA. The solid phase support can then be washed with the buffer a second time to remove unbound antibody. If the antibody is directly labeled, the amount of bound label on solid support can then be detected by conventional means. If the antibody is unlabeled, a labeled second antibody, which detects that antibody that specifically binds RvD1, DHA, or AA can be used.

A solid phase support may be any support capable of binding an antigen or an antibody. Well-known supports or carriers include glass, silocone dioxide or other silanes, polyvinyl, polystyrene, polypropylene, polyethylene, dextran, nylon, amylases, natural and modified celluloses, polyacrylamides, gabbros, hydrogels, gold, platinum, microbeads, micelles and other lipid formations, and magnetite. The nature of the carrier can be either soluble to some extent or insoluble for the purposes of the present disclosure. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet or test strip.

In one embodiment, an enzyme linked immunosorbent assay (ELISA) is utilized to detect the RvD1, DHA, and/or AA (Voller, "The Enzyme Linked Immunosorbent Assay (ELISA)," Diagnostic Horizons 2:1-7, 1978, Microbiological Associates Quarterly Publication, Walkersville, Md.; Voller et al., J. Clin. Pathol. 31:507-520, 1978; Butler, Meth. Enzymol. 73:482-523, 1981; Maggio, (ed.) Enzyme Immunoassay, CRC Press, Boca Raton, Fla., 1980; Ishikawa, et al., (eds.) Enzyme Immunoassay, Kgaku Shoin, Tokyo, 1981). In this method, an enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect RvD1, DHA, and/or AA through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). In another example, a sensitive and specific tandem immunoradiometric assay may be used (see Shen and Tai, J. Biol. Chem., 261:25, 11585-11591, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In some embodiments, the amount of RvD1, DHA, and/or AA present in the biological sample is detected using a RvD1, DHA or AA specific binding agent, such as an antibody or hapten for RvD1, DHA, or AA, which can be detectably labeled. In some embodiments, the specific binding agent is an antibody, such as a polyclonal or monoclonal antibody, that specifically binds RvD1, DHA, or AA. Thus in certain embodiments, determining the amount of RvD1, DHA, or AA in a biological sample includes contacting a biological sample from the subject with a RvD1, DHA, or AA specific binding agent (such as an antibody that specifically binds RvD1, DHA, or AA), detecting whether the binding agent is bound by the sample, and thereby measuring the amount of RvD1, DHA, or AA present in the sample. In certain embodiments, the RvD1, DHA, or AA specific binding agent is an antibody or an antibody fragment that specifically binds RvD1, DHA, or AA. In one embodiment, the specific binding agent is a monoclonal or polyclonal antibody that specifically binds RvD1, DHA, or AA.

An antibody that specifically binds RvD1, DHA, or AA typically binds with an affinity constant of at least $10^7$ M$^{-1}$, such as at least 10.sup.8 M$^{-1}$ at least $5 \times 10^8$ M$^{-1}$ or at least $10^9$ M$^{-1}$. All antibodies that specifically bind RvD1, DHA, or AA now known or yet to be developed are of use in the methods disclosed herein.

The preparation of polyclonal antibodies is well known to those skilled in the art. See, for example, Green et al., "Production of Polyclonal Antisera," in: Immunochemical Protocols pages 1-5, Manson, ed., Humana Press 1992; Coligan et al., "Production of Polyclonal Antisera in Rabbits, Rats, Mice and Hamsters," in: Current Protocols in Immunology, section 2.4.1, 1992.

The preparation of monoclonal antibodies likewise is conventional. See, for example, Kohler & Milstein, Nature 256:495, 1975; Coligan et al., sections 2.5.1-2.6.7; and Harlow et al., in: Antibodies: a Laboratory Manual, page 726, Cold Spring Harbor Pub., 1988. Briefly, monoclonal antibodies can be obtained by injecting mice with a composition including an antigen or a cell of interest, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," in: Methods in Molecular Biology, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane)

prior to injection. After one to three weeks, the desired monoclonal antibody is recovered from the body fluid of the animal.

Antibodies include intact molecules as well as functional fragments thereof, such as Fab, F(ab')2, and Fv and other which are capable of binding the epitopic determinant. These antibody fragments retain some ability to selectively bind with their antigen. Methods of making these fragments are known in the art. (See for example, Harlow and Lane, Antibodies: A Laboratory Manual, Cold Spring Harbor Laboratory, New York, 1988).

Any method known to those of skill in the art can be used to detect and quantify RvD1, DHA, or AA. Thus, in additional embodiments, a spectrometric method is utilized. Spectrometric methods include mass spectrometry, nuclear magnetic resonance spectrometry, and combinations thereof. In one example, mass spectrometry is used to detect the presence of RvD1, DHA, or AA in a biological sample, such as a blood sample, a serum sample, or a plasma sample (see for example, Stemmann, et al., Cell 107 715-726, 2001; Zhukov et al., "From Isolation to Identification: Using Surface Plasmon Resonance-Mass Spectrometry in Proteomics, PharmaGenomics, March/April 2002, available on the PharmaGenomics website on the internet).

RvD1, DHA, or AAalso can be detected by mass spectrometry assays for example coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE) (Kiernan et al., Anal. Biochem. 301, 49-56 (2002); Poutanen et al., Mass Spectrom. 15, 1685-1692 (2001).

The presence of a RvD1, DHA, or AA can be detected with multiple specific binding agents, such as one, two, three, or more specific binding agents. Thus, the methods can utilize more than one antibody. In some embodiments, one of the antibodies is attached to a solid support, such as a multiwell plate (such as, a microtiter plate), bead, membrane or the like. In practice, microtiter plates may conveniently be utilized as the solid phase. The surfaces may be prepared in advance, stored, and shipped to another location(s). However, antibody reactions also can be conducted in a liquid phase.

Mass spectrometry is particularly suited to the identification and quantification of RvD1, DHA, and/or AA from biological samples, such as those descried herein. Typically, mass spectrometers generate gas phase ions from a sample (such as a sample containing RvD1, DHA, and/or AA). The gas phase ions are then separated according to their mass-to-charge ratio (m/z) and detected. Suitable techniques for producing vapor phase ions for use in the disclosed methods include without limitation electrospray ionization (ESI), matrix-assisted laser desorption-ionization (MALDI), surface-enhanced laser desorption-ionization (SELDI), chemical ionization, and electron-impact ionization (EI).

Separation of ions according to their m/z ratio can be accomplished with any type of mass analyzer, including quadrupole mass analyzers (Q), time-of-flight (TOF) mass analyzers (for example linear or reflecting) analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer).

In some embodiments, the mass spectrometric technique is tandem mass spectrometry (MS/MS) and the presence of RvD1, DHA, and/or AA sample is detected. Typically, in tandem mass spectrometry a lipid entering the tandem mass spectrometer is selected and subjected to collision induced dissociation (CID). The spectra of the resulting fragment ion are recorded in the second stage of the mass spectrometry, as a so-called CID spectrum. Suitable mass spectrometer systems for MS/MS include an ion fragmentor and one, two, or more mass spectrometers, such as those described above. Examples of suitable ion fragmentor include, but are not limited to, collision cells (in which ions are fragmented by causing them to collide with neutral gas molecules), photo dissociation cells (in which ions are fragmented by irradiating them with a beam of photons), and surface dissociation fragmentor (in which ions are fragmented by colliding them with a solid or a liquid surface). Suitable mass spectrometer systems can also include ion reflectors.

Prior to mass spectrometry the sample may be subjected to one or more dimensions of chromatographic separation, for example, one or more dimensions of gas, liquid, or size exclusion chromatography. Representative examples of chromatographic separation include paper chromatography, thin layer chromatography (TLC), liquid chromatography, column chromatography, fast protein liquid chromatography (FPLC), ion exchange chromatography, size exclusion chromatography, affinity chromatography, high performance liquid chromatography (HPLC), nano-reverse phase liquid chromatography (nano-RPLC), poly acrylamide gel electrophoresis (PAGE), capillary electrophoresis (CE), reverse phase high performance liquid chromatography (RP-HPLC) or other suitable chromatographic techniques. Thus, in some embodiments, the mass spectrometric technique is directly or indirectly coupled with a liquid chromatography technique, such as column chromatography, fast protein liquid chromatography (FPLC), ion exchange chromatography, size exclusion chromatography, affinity chromatography, high performance liquid chromatography (HPLC), nano-reverse phase liquid chromatography (nano-RPLC), poly acrylamide gel electrophoresis (PAGE), capillary electrophoresis (CE) or reverse phase high performance liquid chromatography (RP-HPLC) to further resolve the biological sample prior to mass spectrometric analysis.

The regents (such as buffers and the like) used in accordance with the disclosed methods are preferable chosen such as to not significantly interfere with mass spectral analysis, such as tandem mass spectrometric methods. Preferably, but not necessarily, the reagents are selected so as to impart desirable characteristics to the analysis. Examples of such characteristics include for example decreasing the energy required to volatilize RvD1, DHA, and/or AA, facilitating ionization, creating predominantly singly charged ions, reducing the peak width, and increasing the sensitivity and/or selectivity of the desired analysis product. .

Following the level of RvD1, DHA, or AA, the results, findings, diagnoses, predictions and/or treatment recommendations can be provided to the subject. For example, the results, findings, diagnoses, predictions and/or treatment recommendations can be recorded and communicated to technicians, physicians and/or patients, pharmacies, or clients. In certain embodiments, computers can be used to communicate such information to interested parties, such as, clients, patients and/or the attending physicians. Based on the measurement, the therapy or protocol administered to a subject can be started, modified not started or re-started. In some examples, the output can provide a recommended therapeutic regimen. In some examples, the test may include determination of other clinical information.

Methods of Treatment of Atherosclerosis and Related Disorders

It is disclosed herein that dysregulated RvD1, DHA, and AA levels are associated with acutely symptomatic carotid disease and stroke. As such, an increase in the level of one or more of RvD1, DHA in patients with of atherosclerosis and related disorders, or a decrease in the level of AA levels in patients with of atherosclerosis and related disorders may be beneficial for inhibiting the development or progression of atherosclerosis and related disorders, such as carotid artery disease, such as arterial plaques, and the rupture thereof.

Methods are disclosed herein for improving vascular function in a subject. The methods include administering to the subject a therapeutically effective amount of an agent administering to the subject an agent that increases the level of RvD1 and/r DHA, or decreases the level of AA in the sera of the subject, thereby improving vascular function. In specific embodiments, the methods include administering to the subject a therapeutically effective amount of an agent that increases the level of RvD1 in the sera of the subject, thereby improving vascular function. In some embodiments, an agent is RvD1 or a derivative thereof.

In some embodiments, the method is a method of treating or stabilizing atherosclerotic plaques in a subject, such as to inhibit atherosclerotic plaque rupture. In some embodiments, the subject has or is suspected of having atherosclerosis. In other embodiments, the subject has had a myocardial infarction, or has intermittent claudication, bowel ischemia, retinal ischemia, transient ischemic attacks (TIAs), ischemic strokes, restenosis after angioplasty, transplant atherosclerosis, unstable angina, or another condition associated with cardiovascular dysfunction.

As used herein, a therapeutically effective amount of a compound is an amount sufficient to result in a biological effect (such as alleviating one or more signs or symptoms of a disease or a condition. For example, an agent can increase the level of RvD1 and/or DHA a desired amount, for example by at least 1.2-fold, at least 1.4-fold, at least 1.6-fold, at least 1.8-fold, at least 2-fold, at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value. In another example, an agent can decrease the level of AA a desired amount, for example by at least 1.2-fold, at least 1.4-fold, at least 1.6-fold, at least 1.8-fold, at least 2-fold, at least 3-fold, at least 4-fold, at least 5-fold, at least 6-fold, at least 8-fold, at least 10-fold, at least 15-fold, at least 20-fold, at least 30-fold or at least 40-fold relative to a control or reference value.

One skilled in the art can readily determine a therapeutically effective amount of an agent to be administered to a given subject by taking into account several factors, such as the size and weight of the subject; the extent of disease progression; the age, health and sex of the subject; the route of administration; and whether the administration is regional or systemic. One skilled in the art can also readily determine an appropriate dosage regimen for administering to a subject the agent.

A therapeutically effective amount of agent can be, for example, the amount necessary to alleviate one or more signs or symptoms of acute arterial plaque rupture or subject to or the amount required to delay progression or a disease, such as atherosclerosis. One of skill in the art can determine the amount of an isolated agent required for therapeutic efficacy.

In some embodiments, a single isolated agent is administered to the subject in need of treatment. In other embodiments, two or more agents (such as 2, 3, 4, 5, 6, 7, 8, 9 or 10 or more) are administered to the subject. When two or more agents are administered to the subject, the agents can be administered simultaneously (or within quick succession, such as within minutes of each other), or they can be administered at different times. For example, two or more agents can be administered one hour, twelve hours, one day, two days, five days, one week, two weeks or one month apart.

One skilled in the art can readily determine an effective amount of a agent to be administered to a given subject, by taking into account factors, such as the size and weight of the subject; the extent of disease progression; the age, health and sex of the subject; the route of administration; and whether the administration is regional or systemic.

For example, an effective amount of an isolated agent can be based on the approximate body weight of a subject to be treated. Any suitable route can administer such effective amounts, such as, for example, intravenous or intraarterial. In some examples, an effective amount of the isolated agent that is administered to a subject can range from about 5 to about 3000 micrograms/kg of body weight, from about 700 to about 1000 micrograms/kg of body weight, or greater than about 1000 micrograms/kg of body weight.

One skilled in the art can also readily determine an appropriate dosage regimen for the administration of an isolated agent to a given subject. For example, an agent can be administered to the subject once (e.g., as a single injection or deposition). Alternatively, an agent can be administered once or twice daily to a subject for a period of from about three to about twenty-eight days, more particularly from about seven to about ten days. In a particular dosage regimen, an agent is administered once a day for seven days. Where a dosage regimen comprises multiple administrations, it is understood that the effective amount of the agent administered to the subject can comprise the total amount of the agent administered over the entire dosage regimen.

Agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization. Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. An appropriate dose can be determined by one of ordinary skill in the art using only routine experimentation.

A therapeutic agent can be administered to a subject by any suitable route. In some examples, the agents are administered using an enteral or parenteral administration route. Suitable enteral administration routes include, for example, oral, rectal, or intranasal delivery. Suitable parenteral administration routes include, for example, intravascular administration (such as intravenous bolus injection, intravenous infusion, intra-arterial bolus injection, intra-arterial infusion and catheter instillation into the vasculature); subcutaneous injection or deposition, including subcutaneous infusion (such as by osmotic pumps); direct application to the tissue of interest, for example by a catheter or other placement device (e.g., a suppository or an implant comprising a porous, non-porous, or gelatinous material); and inhalation. Particularly suitable administration routes are injection, infusion and direct injection into a target tissue.

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

Also disclosed is a method of determining the effectiveness of an agent for treating and/or preventing arterial plaque rupture or an associated inflammation response in a subject. The method including detecting the level of at least one of AA, RvD1 and/or DHA in a sample obtained from the subject following treatment with the agent and comparing the level of at least one of AA, RvD1 and/or to a reference value, wherein an alteration in the level of at least one of AA, RvD1 and/or DHA following treatment indicates that the agent is effective for the agent for treating and/or preventing arterial plaque rupture or an associated inflammation response in the subject. In some embodiments, the reference value the level of at least one of AA, RvD1 and/or DHA in a sample from the subject prior to treatment with the agent.

Kits and Assays

Also provided are kits and assays for determining the level of at least one of AA, RvD1 and/or DHA, for example using a specific biding agent, such as an antibody. In some embodiments, the specific biding agent9s) are labeled, with a detectable label. In some examples, the kits and assays include controls (such as positive and negative controls). In some embodiments, the kits and assays include instructions for the use thereof.

EXAMPLE

This example describes the determination of the ability of specific biomarkers to serve as diagnostic biomarkers of arthrosclerosis.

Study Design

Patients with at least 50% internal carotid artery stenosis undergoing carotid endarterectomy (CEA) were included in this study. For each enrolling patient, the age, sex, history of cardiac disease, chronic renal insufficiency (defined as a serum creatinine 1.6 mg/dL), diabetes, hypertension, and history of tobacco use were recorded, as well as current medication use (antiplatelet, oral hypoglycemic, antihypertensive, or lipid-lowering). Any previous ipsilateral ischemic symptoms, including time from onset were also taken into account. Carotid plaque stability was determined on the basis of presenting symptomatology, confirmed by imaging (magnetic resonance imaging and/or computed tomography angiography imaging of the brain). Asymptomatic patients with high-grade carotid stenosis (≥80% internal carotid stenosis based on duplex ultrasound imaging) were included in the stable or asymptomatic carotid atherosclerotic plaque group. Patients presenting with symptoms of temporary or partial/complete loss of vision, a transient ischemic attack, and/or an established stroke with good neurologic recovery in the index hospitalization and deemed safe to undergo CEA were included as urgent or unstable carotid plaques (H. A. Bazan et al., Annals of vascular surgery, 28 (2014) 1172-1177). The cohort included 24 asymptomatic and 21 acutely symptomatic patients deemed candidates for an urgent carotid endarterectomy (CEA) during the index hospitalization (H. A. Bazan et al., Journal of vascular surgery, 62 (2015) 1529-1538); mean time to intervention for acute interventions was 2.6 days (Table 1).

TABLE 1

Patient demographics.

| Characteristics | Total (n = 45) | Urgent (n = 21) | Asymptomatic (n = 24) | P value |
|---|---|---|---|---|
| Age, year | 65.53 ± 8 | 63.57 ± 6.59 | 67.25 ± 9 | 0.14 |
| Male sex | 28 | 13 | 15 | |
| BMI | 28.16 ± 5.08 | 28.13 ± 5.55 | 28.18 ± 4.75 | 0.97 |
| Total cholesterol mg/dL | 173.79 ± 52.54 | 180 ± 58.91 | 167.82 ± 46.25 | 0.45 |
| HDL mg/dL | 41.79 ± 16.24 | 42 ± 18.09 | 41.36 ± 14.69 | 0.86 |
| LDL mg/dL | 96.21 ± 42.01 | 99.63 ± 46.66 | 92.79 ± 37.7 | 0.61 |
| Triglycerides mg/dL | 184.98 ± 139.77 | 199 ± 146 | 171.32 ± 135.54 | 0.52 |
| Serum creatinine mg/dL | 1.19 ± 0.5 | 1.3 ± 0.61 | 1.09 ± 0.37 | 0.18 |
| Current (all) smoker | 15 (33) | 8 (17) | 7 (16) | |

Lipid Extraction and LC-MS/MS-Based Lipidomic Analysis

The sera were isolated by centrifugation from the fasting peripheral blood of human patients who were identified as urgent/acutely symptomatic and asymptomatic carotid patients. The samples and associated information were de-identified after transfer. The extraction and LC-MS/MS-based lipid mediator analysis were performed following the protocols developed and used previously (see H. A. Bazan et al., Vascul Pharmacol, 51 (2009) 331-336; H. Tian et al., Investigative ophthalmology & visual science, 50 (2009) 3613-3620; Y. Lu et al., Journal of lipid research, 51 (2010) 923-932; H. Tian et al., Journal of cellular biochemistry, 111 (2010) 266-273; H. Tian et al., The Journal of biological chemistry, 286 (2011) 4443-4453; H. Tian et al., Am J Pathol, 179 (2011) 1780-1791; S. Hong et al., The British journal of dermatology, 171 (2014) 30-38; S. Hong et al., Chemistry & biology, 21 (2014) 1318-1329; S. Hong et al., Am J Physiol Cell Physiol, 307 (2014) C1058-1067; S. Hong et al., Journal of immunology, 180 (2008) 3512-3519; N. G. Bazan et al., S. J. Fliesler, O. G. Kisselev (Eds.) Signal Transduction in the Retina, CRC Press, 2007, pp. 345-374; J. D. Morrow et al., Methods in enzymology, 300 (1999) 3-12; E. S. Musiek et al., Journal of chromatography. B, Analytical technologies in the biomedical and life sciences, 799 (2004) 95-102; E. Mas et al., Journal of chromatography. B, Analytical technologies in the biomedical and life sciences, 872 (2008) 133-140. Briefly, deuterium-labeled internal standards [2 ng of each, $d_4$-prostaglandin $D_2$ ($d_4$-PGD2) and $d_5$-DHA in 20 μl methanol] were added to each serum sample (100 μl each) at ~4° C. on water-ice to determine the extraction recoveries (typically >80%) of the lipid mediators. Two volumes of ice-cold LC-MS/MS-grade methanol (EMD Millipore, MA) containing 0.005% butylated hydroxytoluene (BHT, to prevent auto-oxidation) and 0.1 mM acetic acid were added to each serum sample on ice. The mixtures were vortexed for 10 minutes. The supernatants were collected after centrifugation. The pellets were extracted two more times with 200 μl methanol:water (2:1) containing 0.005% BHT and 0.01 mM acetic acid. The extraction supernatants of each serum sample were pooled together and diluted with 10-volume water containing 0.005% BHT and 0.01 mM acetic acid. The mixture of each sample with apparent pH 4.5 was cleaned up with C18 solid phase extraction (500 mg/cartridge, Waters, Milford, Mass.); the cleaned extracts were reconstituted into 50% methanol and analyzed via LC-MS/MS for lipidomic analysis of eicosanoids and docosanoids.

The settings of the LC-MS/MS instrument were as follows. Xevo TQ-S triple quadruple tandem mass spectrometry equipped with Acquity I Class UPLC (Waters) was used. The UPLC was carried out with an Acquity UPLC HSS T3 column (1.8-μm particle size×2.1 inner diameter×50 mm length). At 0.4 ml/min flowrate, the mobile phase ramped from 45% of solvent A ($H_2O$+0.01% acetic acid) and 55% of solvent B (methanol+0.01% acetic acid) to 15% of solvent A and 85% of solvent B in 10 minutes, then ramped to 2% of solvent A and 98% of solvent B in 18 minutes, and then stayed at 2% of solvent A and 98% of solvent B until 25 minutes, and finally changed back to 45% of solvent A and 55% of solvent B and re-equilibrated until 30 minutes passed. The capillary voltage was −2.5 kV. The desolvation temperature was 600° C., and the desolvation gas flowed at 1,100 L/h. The cone gas was 150 L/h, the nebulizer pressure was 7.0 Bars, and ion source temperature was 150° C. Argon collision gas was set at 0.13 mL/min and 3.8 mbar. The injection volume of the coupled autosampler was 10 μL.

LC-MS/MS data were analyzed using MassLynx version 4.1 software (Waters). The compounds in the serum samples were identified by matching the LC multiple reaction monitoring (MRM)-MS/MS ions and chromatographic retention times (within ±0.05 min window) to those of the standards. The mixture of standards was analyzed between every 8-10 sample analyses at the same LC-MS/MS conditions as the sample analysis. The extraction recovery was determined using the deuterium-labeled internal standards. The quantities of compounds were calculated from areas of identified LC MRM-MS/MS chromatographic peaks, extraction recoveries, and calibration curves of compound standards. The concentrations (pico-molar, or pMs) of these lipids in sera (100 μL each) were then calculated. The identification of analytes was also confirmed by the full scan MS/MS spectra and LC chromatographic retention times acquired from samples via LC-full scan MS/MS after comparing with the standard compound.

RvD1, DHA, AA were purchased from caymanchem.com (Cayman Chemical, Ann Arbor, Mich.) and used as external standards for the tuning, calibration, and other optimization of LC-MS/MS equipment. Deuterium-labeled $d_4$-prostaglandin $D_2$ ($d_4$-$PGD_2$) and $d_5$-DHA from Cayman Chemical were used as the internal standards to determine the recoveries of lipid extraction and quantities of the analytics in LC-MS/MS analysis.

Statistical Analysis

All data were presented in average±standard error of the mean (SEM) and analyzed using analysis of variance (ANOVA) tests. A p-value of ≤0.05 was considered statistically significant. Logistic regression was used for multi-variable analysis. SPSS software (available on the world wide web at ibm.com) was used for the statistical analysis. Logistic regression was used for ROC analysis. Modeling and calculation of related area under curve (AUC), sensitivity/specificity, positive likelihood ratio (LR+), negative LR (LR−), and accuracy were carried out in SAS and R software packages.

Results

Optimization of LC-MS/MS for Lipidomic Analysis of Patients' Sera

Figure 2:
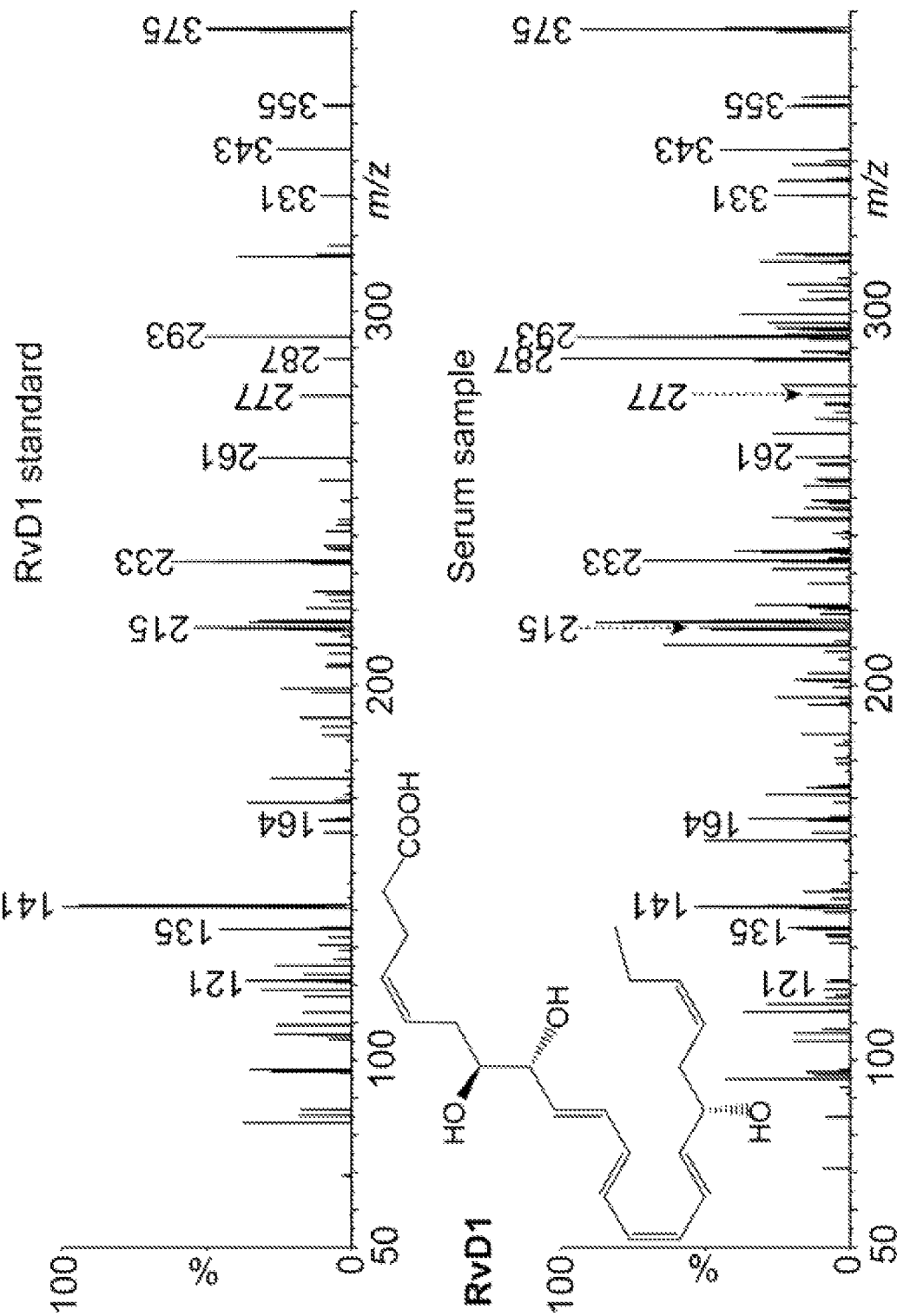
FIG. 2 is a MS/MS full scan spectra of RvD1, the omega-3 polyunsaturated fatty acid (DHA), and the omega-6 polyunsaturated fatty acid arachidonic acid (AA) acquired from an asymptomatic patient's sera using multiple reaction monitoring (MRM) LC-MS/MS.

There were no differences between the two patient groups' demographics (Table 1). Lipid mediators were extracted using methanol and solid phase extraction (SPE) technique as descried previously (H. Tian et al., The Journal of biological chemistry, 286 (2011) 4443-4453). SPE usually yields better recovery and cleanup of analysts than liquid-liquid extraction alone. LC MRM-MS/MS methodology was used to analyze the serum extracts because it offers high sensitivity, reproducibility, and selectivity to analyze small molecules, including the compounds targeted in this Example (see J. M. Poczobutt et al., PloS one, 8 (2013) e79633; J. Claria et al., Am J Physiol Cell Physiol, 304 (2013) C1141-1149; R. C. Poulsen et al., American journal of hematology, 83 (2008) 437-445; L. Belayev et al., Transl Stroke Res, 2 (2011) 33-41; N. G. Bazan et al., Exp Neurol, 236 (2012) 122-130). Table 2 and FIG. 1 present the optimized MRM parent ions in Q1 sector, signature daughter ions in Q3 sector, cone voltages, collision voltages, and LC MRM-MS/MS retention times for each compound that, together, yielded the best sensitivity and reproducibility in analysis of inflammation-resolving resolvin D series and lipoxin $A_4$, as well as their respective precursors DHA and AA. The optimization provided each compound a unique set of parameters that were different from those of other compounds (Table 2 and FIG. 1), which allowed for the specific detection of each compound by LC MRM-MS/MS. The identification of RvD1 in sera was verified further by an MS/MS full-scan spectrum acquired from a larger volume of sera of patients (FIG. 2), which possessed diagnostic MS/MS ions of RvD1 as showed in the MS/MS spectrum of resolving D1 standard.

TABLE 2

Major parameters of multiple reaction monitoring (MRM) analysis for mediator-targeted lipidomics using LC-MS/MS.

| Compound | MRM parent or Q1 ion, m/z | MRM daughter or Q3 ions, m/z | Cone (V) | Collusion (V) |
|---|---|---|---|---|
| AA | 303.2 | 259.4 | 50 | 12 |
| DHA | 327.2 | 283.4 | 2 | 14 |
| RvD1 | 375.2 | 121.1 | 2 | 26 |
|  |  | 141.1 | 2 | 14 |

Resolvin D1 and Ratio of Arachidonic Acid:Resolvin D1 or Arachidonic Acid:Docosahexaenoic Acid: Serum Biomarkers for Diagnosis of Acutely Symptomatic Carotid Plaques.

Following the widely-used methodology to identify small molecules, including lipid mediators in the picogram range in physiopathological specimen (see J. M. Poczobutt, M et al., PloS one, 8 (2013) e79633; J. Claria et al., Am J Physiol Cell Physiol, 304 (2013) C1141-1149; R. C. Poulsen et al., American journal of hematology, 83 (2008) 437-445; L. Belayev et al., Transl Stroke Res, 2 (2011) 33-41; N. G. Bazan et al., Exp Neurol, 236 (2012) 122-130), the criterion was used that the compounds identified in a patient's sera must have their LC MRM-MS/MS chromatographic retention times (within ±0.1 min window) and signature MRM product ions match to those of the authentic standards. RvD1 was identified by this criterion (FIG. 1 and Table 2). However, other resolvins and lipoxin $A_4$ were only detected when their amounts reached the minimal detection limits in one or two samples, thus they were not considered for biomarker potentials. DHA and AA were also identified in abundant quantities in sera (FIG. 1).

RvD1, AA, and DHA were next quantified based on their LC MRM-MS/MS chromatographic peak areas, extraction recoveries, and linear calibration curves (Table 3).

LC MRM-MS/MS chromatographic peak quantification of RvD1, AA, and DHA revealed that sera RvD1 concentrations were 82±11 pM for acutely symptomatic (urgent) vs. 152±17 pM for asymptomatic carotid patients (p=0.001). Additionally, DHA (precursor of RvD1 biosynthesis) was lower in the sera of urgent, compared to asymptomatic carotid patients (52081±6704 pM versus 75771±7638 pM, p=0.025). However, the serum concentration of AA, a major n-6 PUFA, was higher in asymptomatic vs. urgents (429188±46484 pM versus 257442±35135 pM, p<0.01). RvD1 concentration provided the strongest correlation for urgent status (p<0.01); high levels occurred in stable plaques, while low levels occurred in the acute rupture.

TABLE 3

Sera concentrations of select inflammation-resolving lipid mediators and omega-3 (DHA) and omega-6 (AA) PUFAs quantified by LC-MS/MS.

| Lipids | Urgent (pM) | Asymptomatic | P-value |
|---|---|---|---|
| AA (C20:4-n6) | 429188 +/− 46484 | 429188 +/− 46484 | 0.005 |
| DHA (C22:6-n3) | 52081 +/− 6704 | 75771 +/− 7638 | 0.025 |
| RvD1 | 82 +/− 11 | 429188 +/− 46484 | 0.001 |

Notes:
Results are mean +/− SEM, 21 acute patients and 24 asymptomatic patients;
pM: picomolar/L seruym.

Next, it was investigated whether the sera concentration ratio of AA:DHA, AA:RvD1, and DHA:RVD1 could discern differences between the urgent and asymptomatic groups.

Figure 3A:
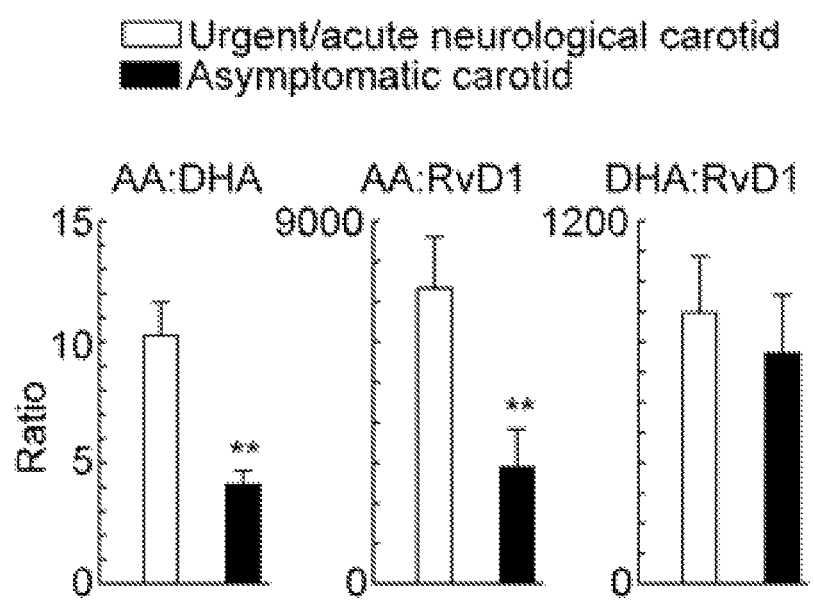
Figure 3B:
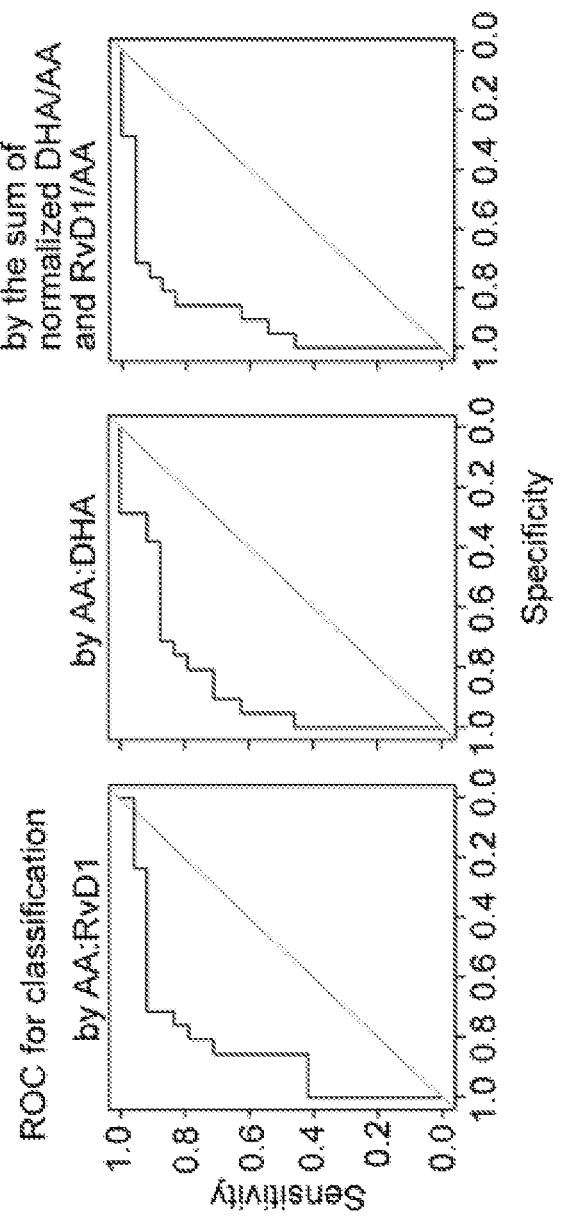

To investigate whether the concentration ratio of AA:DHA, AA:RvD1, DHA:RVD1, in the sera also could manifest differences between the acutely symptomatic and asymptomatic groups, these ratios were compared. The ratios of AA:DHA and AA:RvD1 were associated with urgent; both were higher in the sera of acutely symptomatic patients (10.3±1.4 versus 4.1±0.6, p<0.01 and 7331.0±1280.8 versus 2897.4±932.0, p<0.01, respectively), whereas there was no significant difference for DHA:RvD1 (FIG. 3A). Moreover, to determine whether the concentration ratio of AA:RvD1 or AA:DHA has an ability to predict the acute symptom of the carotid, the predictive values of AA:RvD1, AA:DHA, RvD1, AA, and DHA were evaluated by ROC curve analysis. The areas under the ROC curve (AUC) for predicting carotid plaque rupture were in descending order: 0.8611 (0.7525, 0.9698, 95% CI) for AA:DHA; 0.8353 (0.7097-0.9609, 95% CI) for AA:RvD1; 0.7619 (0.6178, 0.9061, 95% CI) for RvD1; 0.756 (0.6122, 0.8997, 95% CI) for AA; 0.6905 (0.5312, 0.8497, 95% CI) for DHA; and 0.5595 (0.3804, 0.7387, 95% CI) for DHA:RvD1 (FIGS. 3B and 3C). The p values show that these concentrations of AA, DHA, and RvD1 as well as their concentration ratios had AUC significantly greater than 50% (classification by chance). Both AUC and accuracy show that AA:DHA and AA:RvD1 perform best. Further comparisons show that the AUCs of AA:DHA and AA:RvD1 were not significantly different (p value=0.72), but they were significantly different from that of DHA:RvD1 (p values=0.0121 and 0.0002). The AUCs of DHA, AA, RvD1 were not significantly different (p values: 0.6147 for AA vs DHA; 0.4636 for DHA vs RvD1). More interestingly, it was found that combining two concentration ratios improved the ability of predicting carotid plaque rupture. Using the sum of the Z scores of DHA:AA and the Z scores of RvD1:AA in ROC analysis, the AUC increases to 0.8988 (0.8069, 0.9907, 95% CI), which is significantly greater than 50%. This combination provides a powerful multi-parameter prediction tool.

Discussion

Unresolved chronic inflammation is a major factor in atherosclerotic plaque rupture. Resolvins are endogenous inflammation-resolving lipid mediators that are triggered by inflammation, likely as a self-defense action. In instances where resolvins are not adequately expressed, a pro-inflammatory state dominates (see G. Fredman et al., Nature communications, 7 (2016) 12859; E. Titos et al., Tissue, Journal of immunology, 197 (2016) 3360-3370; H. M. Hsiao et al., The American journal of pathology, 185 (2015) 3189-3201; K. S. Rathod et al., The Journal of clinical investigation, 127 (2017) 169-182). Furthermore, in the case of atherosclerosis, inflammation is a component that is associated with the development of atherosclerotic plaque rupture (P. Libby et al., Circulation, 105 (2002) 1135-1143; G. Fredman et al., Nature communications, 7 (2016) 12859). As disclosed herein is was demonstrates that circulating resolvin levels correspond to carotid plaque stability. Utilizing a translational model of plaque rupture (see H. A. Bazan, et al., Stroke; a journal of cerebral circulation, 46 (2015) 3285-3287), serum levels of RvD1 and DHA, a precursor of RvD1, were found to be markedly lower in patients presenting with acutely symptomatic plaque rupture events compared to patients with asymptomatic carotid disease. This correlates with the inventors previous work demonstrating that acutely symptomatic plaques have a decreased content of anti-inflammatory lipids, such as DHA (H. A. Bazan et al., Vascul Pharmacol, 51 (2009) 331-336). Additionally AA, the major ω6 PUFA in human blood, was detected at higher levels in the sera of acutely symptomatic compared to asymptomatic carotid patients, consistent with the heightened chronic inflammation mediated by AA as the original source of several key inflammatory lipid mediators, including leukotrienes.

As the inventors searched for a biomarker of plaque rupture, the concentration ratio of AA:RvD1 (pM:pM) in the sera was initially chosen because this incorporates the AA and RvD1 differences noted between the acutely symptomatic and asymptomatic carotid patients. This was confirmed by the observation that the AA:RvD1 ratio was significantly higher for asymptomatic patients than for acutely symptomatic patients (FIG. 3A). The serum concentration ratio of AA:DHA had a similar trend. These ratios are unitless and dimensionless, which reduces the systematic errors in the analysis of the lipids. Additionally, the ratio uses one value instead of two values, which could simplifies the presentation of the lipid mediators in the patient sera. To further examine the predictive values of RvD1, AA, DHA, AA:RvD1, and AA:DHA, ROC curve analysis was performed to calculate the sensitivity and specificity in the differentiation of the acutely symptomatic from the asymptomatic carotid patients. This analysis indicated that AA:RvD1, RvD1, AA:DHA, DHA, or AA are diagnostic biomarkers. However, AA:DHA and AA:RvD1 had the highest AUC in ROC demonstrating that they are likely the best biomarkers.

A power analysis shows that at 5% significance level, the cohort of 21 acutely symptomatic and 24 asymptomatic patients has a relative high power to detect the effect size in most lipid mediators and ratios. Specifically, there is a power of: 0.92 for RvD1 samples, 0.82 for AA samples, 0.62 for DHA samples, 0.98 for the ratio of AA:DHA, 0.78 for the ratio of AA:RvD1, but low power of 0.08 for the ratio of DHA:RvD1.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention claimed is:

1. A kit for detecting arachidonic acid (AA), resolvin D1 (RvD1), and docosahexaenoic acid (DHA), in a biological sample, comprising:
   a solid phase support capable of immobilizing AA, RvD1, and DHA;
   a first specific binding agent that specifically binds to AA, a second specific binding agent that specifically binds to RvD1, and a third specific binding agent that specifically binds to DHA; and
   detectable labels that couple directly or indirectly to each of the first specific binding agent, the second specific binding agent, and the third specific binding agent for quantification of a ratio of both AA:DHA and AA:RvD1 in the biological sample.

2. The kit of claim 1, wherein the first specific binding agent is labeled with a first detectable label, the second specific binding agent is labeled with a second detectable label, and the third specific binding agent is labeled with a third detectable label.

3. An assay for detecting arachidonic acid (AA), resolvin D1 (RvD1), and docosahexaenoic acid (DHA) in a biological sample of a subject, comprising:
   a first specific binding agent that specifically binds to AA, a second specific binding agent that specifically binds to RvD1, and a third specific binding agent that specifically binds to DHA, wherein the first specific binding agent is labeled directly or indirectly with a first detectable label, the second specific binding agent is labeled directly or indirectly with a second detectable label, and the third specific binding agent is labeled directly or indirectly with a third detectable label; and
   wherein the first detectable label, the second detectable label, and the third detectable label are used to quantify a ratio of both of AA:DHA and AA:RvD1 in the biological sample.

4. The kit of claim 1, further comprising a first secondary antibody labeled with a fourth detectable label, the first secondary antibody capable of specifically binding the first specific binding agent;
   a second secondary antibody labeled with a fifth detectable label, the second secondary antibody capable of specifically binding the second specific binding agent; and
   a third secondary antibody labeled with a sixth detectable label, the third secondary antibody capable of specifically binding the third specific binding agent.

5. The kit of claim 1, wherein one or more of the first specific binding agent is a first monoclonal or polyclonal antibody, the second specific binding agent is a second monoclonal or polyclonal antibody, and the third specific binding agent is a third monoclonal or polyclonal antibody.

6. The kit of claim 1, wherein one or more of the first specific binding agent is a first hapten, the second specific binding agent is a second hapten, and the third specific binding agent is a third hapten.

7. The kit of claim 1, wherein the solid phase support is selected from the group consisting of glass, silicone dioxide or other silanes, polyvinyl, polystyrene, polypropylene, polyethylene, dextran, nylon, amylases, natural and modified celluloses, polyacrylamides, gabbros, hydrogels, gold, platinum, microbeads, micelles and other lipid formations, and magnetite; and
  wherein the solid phase support is configured as spherical, cylindrical, or flat.

8. The kit of claim 1, wherein the solid phase support further comprises a fourth specific binding agent that specifically binds to AA, a fifth specific binding agent that specifically binds to RvD1, and a sixth specific binding agent that specifically binds to DHA.

9. The kit of claim 1, adapted for an Enzyme-linked ImmunoSorbent Assay (ELISA).

10. The kit of claim 1, further comprising one or more of a standard or a set of standards for use in comparing to levels of AA, RvD1, and DHA, or ratios of AA:RvD1 and AA:DHA in the biological sample; a wash buffer; and instructions for use.

11. The kit of claim 1, further comprising written instructions for the detection or prediction of an acutely symptomatic carotid plaque rupture event based on the ratio of both AA:RvD1 and AA:DHA in the biological sample.

12. The kit of claim 1, wherein the biological sample is blood or a component of blood including serum or plasma.

13. The assay of claim 3, wherein AA, DHA, and RvD1 are immobilized on a solid support.

14. The assay of claim 3, wherein the first specific binding agent, the second specific binding agent and the third specific binding agent are selected from the group consisting of monoclonal antibodies, polyclonal antibodies, or haptens.

15. The assay of claim 3, wherein the first detectable label, the second detectable label, and the third detectable label are selected from the group consisting of enzymes, fluorophores, radioactive isotopes, and chemiluminescent compounds.

16. The assay of claim 3, further comprising written instructions for the detection or prediction of acutely symptomatic carotid disease in the subject based on the ratio of AA:RvD1 and AA:DHA in the biological sample as determined via the assay, the written instructions including a first reference value corresponding to the ratio of AA:DHA, and a second reference value corresponding to the ratio of AA:RvD1; and
  wherein the ratio of AA:DHA greater than the first reference value and the ratio of AA:RvD1 greater than the second reference value indicates, in accordance with the written instructions, the detection or prediction of the acutely symptomatic carotid disease in the subject.

17. The assay of claim 16, wherein the first reference value is between 6 and 8; and wherein the second reference value is between 5000 and 6000.

18. The assay of claim 3, wherein the biological sample is blood or a component of blood including serum or plasma.

* * * * *